United States Patent
Failli et al.

[11] Patent Number: 5,162,333
[45] Date of Patent: Nov. 10, 1992

[54] AMINODIESTERS OF RAPAMYCIN

[75] Inventors: Amedeo A. Failli, Princeton Junction, N.J.; Robert J. Steffan, Langhorne, Pa.

[73] Assignee: American Home Products Corporation, New York, N.Y.

[21] Appl. No.: 757,858

[22] Filed: Sep. 11, 1991

[51] Int. Cl.$^5$ ............... A61K 31/395; C07D 498/08
[52] U.S. Cl. ........................ 514/291; 540/456
[58] Field of Search ................ 540/456; 514/291

[56] References Cited

U.S. PATENT DOCUMENTS

| | | | |
|---|---|---|---|
| 3,929,992 | 12/1975 | Sehgal et al. | 424/129 |
| 3,993,749 | 11/1976 | Sehgal et al. | 424/122 |
| 4,316,885 | 2/1982 | Rakhit | 424/122 |
| 4,401,653 | 8/1983 | Eno | 425/114 |
| 4,650,803 | 3/1987 | Stella et al. | 514/291 |
| 4,885,171 | 12/1989 | Sehgal et al. | 424/122 |

OTHER PUBLICATIONS

J. Antibiot. 28, 721–726 (1975).
J. Antibiot. 28, 727–732 (1975).
J. Antibot. 31, 539–545 (1978).
Can. J. Physiol. Pharmacol. 55, 48 (1977).
FASEB 3, 3411 (1989).
FASEB 3, 5256 (1989).
Lancet 1183 (1978).
Med. Sci. Res. 17: 877 (1989).

*Primary Examiner*—Robert T. Bond
*Attorney, Agent, or Firm*—Arnold S. Milowsky

[57] ABSTRACT

A compound of the structure

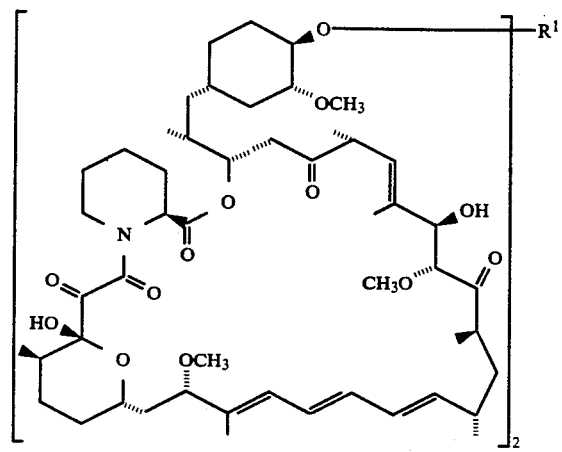

wherein $R^1$ is

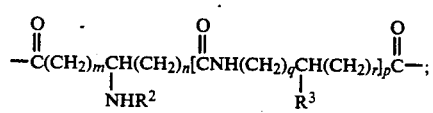

$R^3$ is hydrogen, alkyl, arylalkyl, $(CH_2)_sNR^4R^5$, aminoalkyl, hydroxyalkyl, guanylalkyl, mercaptoalkyl, alkylthioalkyl, indolylmethyl, hydroxyphenylmethyl, imidazolylmethyl or phenyl which is optionally mono-, di-, or tri-substituted;

$R^4$ is hydrogen, alkyl, or aralkyl;

$R^2$ and $R^5$ are each independently hydrogen, formyl, alkanoyl, arylalkanoyl, aryloyl, or $CO_2R^6$;

$R^6$ is alkyl, arylalkyl, allyl, fluorenylmethyl, or phenyl which is optionally mono-, di-, or tri-substituted;

m is 0–4; n is 0–4; p is 0–1; q is 0–4; r is 0–4; and s is 0–4; or a pharmaceutically acceptable salt thereof, which by virtue of its immunosuppressive activity is useful in treating transplantation rejection, host vs. graft disease, autoimmune diseases, and diseases of inflammation, by virtue of its antifungal activity is useful in treating fungal infections; and by virtue of its antitumor activity is useful in treating tumors.

7 Claims, No Drawings

AMINODIESTERS OF RAPAMYCIN

BACKGROUND OF THE INVENTION

This invention relates to novel esters of rapamycin and a method for using them in the treatment of transplantation rejection, host vs. graft disease, autoimmune diseases, diseases of inflammation, tumors, and fungal infections.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Seghal et al., J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). The ability of rapamycin to prolong survival time of organ grafts in histoincompatible rodents was disclosed by Morris. [Med. Sci. Res. 17: 877 (1989)]. Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Calne et al., Lancet 1183 (1978)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42-positions.

DESCRIPTION OF THE INVENTION

This invention provides derivatives of rapamycin which are useful as immunosuppressive, anti-inflammatory, antitumor, and antifungal agents having the structure

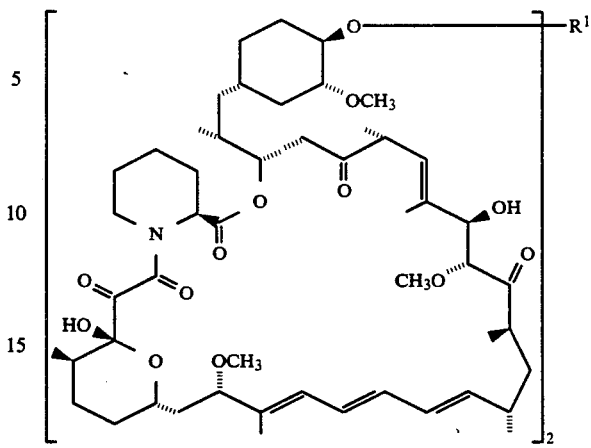

wherein $R^1$ is

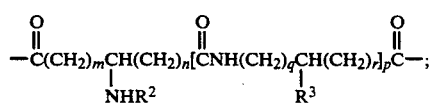

$R^3$ is hydrogen, alkyl of 1–6 carbon atoms, arylalkyl of 7–10 carbon atoms, $(CH_2)_sNR^4R^5$, aminoalkyl of 1–4 carbon atoms, hydroxyalkyl of 1–4 carbon atoms, guanylalkyl of 2–4 carbon atoms, mercaptoalkyl of 1–4 carbon atoms, alkylthioalkyl of 2–6 carbon atoms, indolylmethyl, hydroxyphenylmethyl, imidazolylmethyl or phenyl which is optionally mono-, di-, or tri-substituted with a substituent selected from alkyl of 1–6 carbon atoms, alkoxy of 1–6 carbon atoms, hydroxy, cyano, halo, nitro, carbalkoxy of 2–7 carbon atoms, trifluoromethyl, amino, or a carboxylic acid;

$R^4$ is hydrogen, alkyl of 1–6 carbon atoms, or aralkyl of 7–10 carbon atoms;

$R^2$ and $R^5$ are each independently hydrogen, formyl, alkanoyl of 2–7 carbon atoms, arylalkanoyl of 8–11 carbon atoms, aryloyl, or $CO_2R^6$;

$R^6$ is alkyl of 1–6 carbon atoms, arylalkyl of 7–10 carbon atoms, allyl, fluorenylmethyl, or phenyl which is optionally mono-, di-, or tri-substituted with a substituent selected from alkyl of 1–6 carbon atoms, alkoxy of 1–6 carbon atoms, hydroxy, cyano, halo, nitro, carbalkoxy of 2–7 carbon atoms, trifluoromethyl, amino or a carboxylic acid;

m is 0–4;
n is 0–4;
p is 0–1;
q is 0–4;
r is 0–4; and
s is 0–4 or a pharmaceutically acceptable salt thereof.

Of the compounds, preferred members are those in which p is 0; and those in which p is 0, m is 0, and n is 1–2.

Aryl is defined as an organic radical derived from an aromatic hydrocarbon by the removal of one atom; e.g., phenyl from benzene. Arylalkyl is defined as an arylated alkyl radical; a radical in which an alkyl H atom is substituted by an aryl group. The definition of aryl and arylalkyl are also intended to encompass compounds in which the phenyl groups of such moieties are optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, a carboxylic acid, or the like.

The pharmaceutically acceptable salts may be formed from inorganic cations such as sodium, potassium, and the like; mono-, di-, and trialkyl amines of 1-6 carbon atoms, per alkyl group and mono-, di-, and trihydroxyalkyl amines of 1-6 carbon atoms per alkyl group; and organic acids such as acetic, lactic, citric, tartaric, succinic, maleic, malonic, gluconic, and the like.

The compounds of this invention can be prepared by acylating rapamycin with an acylating agent having the general structure

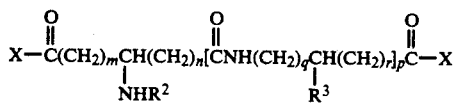

where $R^2$, $R^3$, m, n, p, q, and r are as defined above, and X is OH, in the presence of a coupling agent, such as dicyclohexylcarbodiimide, or a water soluble carbodiimide. The compounds of this invention also can be prepared using a mixed anhydride, or an activated ester of the above described carboxylic acid (such as those with p-nitrophenol, pentachloro or pentafluorophenol, 2,4,5-trichlorophenol, N-hydroxysuccinimide, N-hydroxyphthalimide or 1-hydroxy-1H-benzotriazole) as the acylating species. Alternatively the acylating species can be an acid halide, where X can be Cl, Br or F (except when $R^2$ or $R^6$=t-Bu), an azide or an imidazolide derivative of said acid.

The acylating groups used to prepare the compounds of this invention are commercially available or can be prepared by methods that are disclosed in the literature. The amino acids used to prepare the compounds of this invention can have either the R or S configuration, and the optically active carbon will retain its relative configuration when transformed into a compound of this invention. Where p is 1 the acylating species can typically be prepared by condensing two amino acids to form a dipeptide which is transformed into the acylating species illustrated above by standard chemical methodology.

Immunosuppressive activity was evaluated in an in vitro standard pharmacological test procedure to measure lymphocyte proliferation (LAF) and in two in vivo standard pharmacological test procedures. The first in vivo procedure was a popliteal lymph node (PLN) test procedure which measured the effect of compounds of this invention on a mixed lymphocyte reaction and the second in vivo procedure evaluated the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated; radioactivity is determined. Inhibition of lymphoproliferation is assessed in percent change in counts per minute from non-drug treated controls. The results are expressed by the following ratio, or as the $IC_{50}$, expressed in nM.

$$\frac{^3\text{H-control thymus cells} - ^3\text{H-rapamycin-treated thymus cell}}{^3\text{H-control thymus cells} - ^3\text{H-test compound-treated cells}}$$

A mixed lymphocyte reaction (MLR) occurs when lymphoid cells from genetically distinct animals are combined in tissue culture. Each stimulates the other to undergo blast transformation which results in increased DNA synthesis that can be quantified by the incorporation of tritiated thymidine. Since stimulating a MLR is a function of disparity at Major Histocompatibility antigens, an in vivo popliteal lymph node (PLN) test procedure closely correlates to host vs. graft disease. Briefly, irradiated spleen cells from BALB/c donors are injected into the right hind foot pad of recipient C3H mice. The drug is given daily, p.o. from Day 0 to Day 4. On Day 3 and Day 4, tritiated thymidine is given i.p., b.i.d. On Day 5, the hind popliteal lymph nodes are removed and dissolved, and radioactivity counted. The corresponding left PLN serves as the control for the PLN from the injected hind foot. Percent suppression is calculated using the non-drug treated animals as allogenic control. Rapamycin at a dose of 6 mg/kg, p.o. gave 86% suppression, whereas cyclosporin A at the same dose gave 43% suppression. Results are expressed by the following ratio:

$$\frac{^3\text{H-PLN cells control C3H mouse} - ^3\text{H-PLN cells rapamycin-treated C3H mouse}}{^3\text{H-PLN cells control C3H mouse} - ^3\text{H-PLN cells test compound-treated C3H mouse}}$$

The second in vivo test procedure is designed to determine the survival time of pinch skin graft from male DBA/2 donors transplanted to male BALB/c recipients. The method is adapted from Billingham R. E. and Medawar P. B., J. Exp. Biol. 28:385-402, (1951). Briefly, a pinch skin graft from the donor is grafted on the dorsum of the recipient as a homograft, and an autograft is used as control in the same region. The recipients are treated with either varying concentrations of cyclosporin A as test control or the test compound, intraperitoneally. Untreated recipients serve as rejection control. The graft is monitored daily and observations are recorded until the graft becomes dry and forms a blackened scab. This is considered as the rejection day. The mean graft survival time (number of days±S.D.) of the drug treatment group is compared with the control group.

The following table summarizes the results of representative compounds of this invention in these three standard test procedures.

TABLE 1*

| Compound | LAF $IC_{50}$ (nM) | LAF (ratio) | PLN (ratio) | Skin Graft (days ± SD) |
|---|---|---|---|---|
| Example 1 | 16.50 | 0.53 | 0.45 | 10.2 ± 0.4 |
| Example 2 | 27.40 | 0.32 | 0.45 | 10.7 ± 0.2 |
| Rapamycin | 8.70 | | | 12.0 ± 1.7 |

*Calculation of ratios was described supra.

The results of these standard pharmacological test procedures demonstrate immunosuppressive activity both in vitro and in vivo for the compounds of this invention. Positive ratios in the LAF and PLN test procedures indicate suppression of T cell proliferation.

As a transplanted pinch skin grafts are typically rejected within 6–7 days without the use of an immunosuppressive agent, the increased survival time of the skin graft when treated with the compounds of this invention further demonstrates their utility as immunosuppressive agents.

Based on the results of these standard pharmacological test procedures, the compounds are useful in the treatment of transplantation rejection such as, heart, kidney, liver, bone marrow, and skin transplants; autoimmune diseases such as, lupus, rheumatoid arthritis, diabetes mellitus, myasthenia gravis, and multiple sclerosis; and diseases of inflammation such as, psoriasis, dermatitis, eczema, seborrhea, inflammatory bowel disease. Because the compounds are structurally related to rapamycin and have a similar immunosuppressive activity profile to rapamycin, the compounds of this invention are considered to have antitumor and antifungal activities.

The compounds may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

In addition, the compounds of this invention may be employed as a solution, cream, or lotion by formulation with pharmaceutically acceptable vehicles containing 0.1–5 percent, preferably 2%, of active compound which may be administered topically.

The following examples illustrate the preparation of representative compounds of this invention.

Rapamycin-42,42'-diester with N-[(phenylmethoxy)carbonyl]-L-glutamic acid

Under an atmosphere of nitrogen, a solution of rapamycin (0.914 g, 1 mmole), $N^\alpha$-benzyloxycarbonyl-L-glutamic acid (0.14 g, 0.5 mmole), dicyclohexylcarbodiimide (0.2 g, 1 mmole) and 4-dimethylaminopyridine (0.12 g, 1 mmole) in 10 mL of dichloromethane is stirred at room temperature for 72 hours. The crude product is purified twice by flash chromatography (on silica Merck 60, using hexane-ethyl acetate 1:1 and hexane-ethyl acetate 2:1 respectively) to yield 0.14 g of the title compound as a white solid.

$^1$H NMR (CDCl$_3$, 400 MHz): δ 1.655 (s, 6H, CH$_3$C=C), 1.753 (s, 6H, CH$_3$C=C), 3.14 (s, 6H, CH$_3$O), 3.33–3.38 (m, 12H, CH$_3$O), 4.18 (2s, 2H, 31,31'—CH), 5.10 (s, 2H, CH$_2$Ph), 7.35 (s, 5H, PhH);

MS (neg. ion FAB, m/z): 2073 (M-H)$^-$, 590;

Anal. Calcd for C$_{115}$H$_{169}$N$_3$O$_{30}$: C, 66.61; H, 8.22; N, 2.03; Found: C, 66.01; H, 8.28; N, 2.36.

The following representative compounds can be prepared from rapamycin and the appropriate amino diacid by employing the method used to prepare the title compound in Example 1.

Rapamycin-42,42'-diester with N-ethanoyl-L-glutamic acid

Rapamycin-42,42'-diester with N-formyl-L-aspartic acid

Rapamycin-42,42'-diester with N-benzoyl-L-aspartic acid

Rapamycin-42,42'-diester with N-[(phenylethyl)carbonyl]-L-glutamic acid

Rapamycin-42,42'-diester with 3-aminoadipic acid

Rapamycin-42,42'-diester with 4-(N-benzoylamino)octan-1,8-dioic acid

Rapamycin-42,42'-diester with 4-[(N-(ethoxy)carbonyl)amino]adipic acid

Rapamycin-42,42'-diester with N-[(fluorenylmethoxy)carbonyl]-L-aspartyl-L-histidine Rapamycin-42,42'-diester with N-[(3',4',5'-trihydroxyphenoxy)carbonyl]-L-glutamyl-D-alanine Rapamycin-42,42'-diester with N-[allyloxy)carbonyl]-D-aspartyl-L-serine Rapamycin-42,42'-diester with N-[(phenylmethoxy)carbonyl]-D-glutamyl-L-methionine Rapamycin-42,42'-diester with N-[(phenylmethyl)oxo]-L-glutamyl-L-threonine

EXAMPLE 2

Rapamycin 42-42'-diester with N-[(phenylmethoxycarbonyl)]-L-aspartic acid

Under a nitrogen atmosphere, a solution of Rapamycin (0.914 g, 1 mmole), $N^\alpha$-benzyloxycarbonyl-L-aspartic acid (0.133 g, 0.5 mmole), dicyclohexylcarbodiimide (0.2 g, 1 mmole), and 4-dimethylaminopyridine (0.12 g, 1 mmole) in 10 mL of dichloromethane is stirred at room temperature for 72 hours. The reaction mixture is then concentrated in vacuo and the residue is prepurified through a 5×20 mm plug of silica gel by elution with EtOAc. The eluate is evaporated to yield a yellow solid foam which is further purified by HPLC (using a Dynamax 60A silica 8μ 41×300 mm column, ethyl acetate-hexane gradient from 1:1 to 2:1, flow rate 30 mL/min) to provide the title compound (0.16 g) as a white solid.

$^1$H NMR (CDCl$_3$, 400 MHz): δ 1.652 (s, 6H, CH$_3$C=C), 1.748 (s, 6H, CH$_3$C=C), 3.138 (s, 6H, CH$_3$O), 3.33 (m, 12H, CH$_3$O), 4.17 (2s, 2H, 31-31'—CH), 5.11 (s, 2H, CH$_2$Ph)), 7.34 (s, 5H, PhH);

MS (neg.ion FAB,m/z): 2058 (M-H)$^-$, 590.

What is claimed is:

1. A compound of the formula

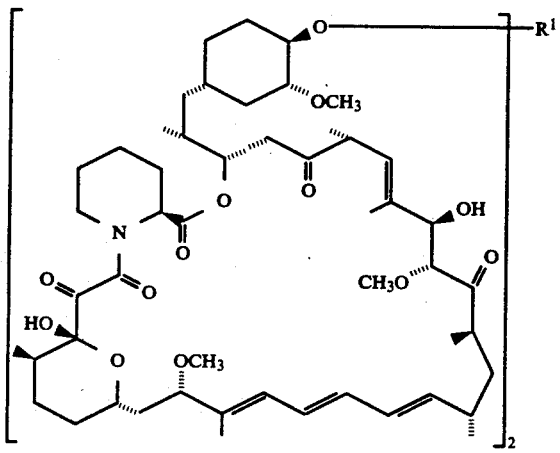

wherein R$^1$ is

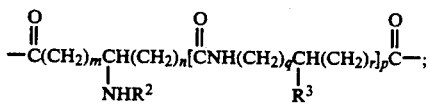

R$^3$ is hydrogen, alkyl of 1-6 carbon atoms, phenylalkyl of 7-10 carbon atoms, (CH$_2$)$_s$NR$^4$R$^5$, aminoalkyl of 1-4 carton atoms, hydroxyalkyl of 1-4 carbon atoms, guanylalkyl of 2-4 carbon atoms, mercaptoalkyl of 1-4 carbon atoms, alkylthioalkyl of 2-6 carbon atoms, indolylmethyl, hydroxyphenylmethyl, imidazolylmethyl or phenyl; wherein the phenyl moiety of the phenyl and phenylalkyl groups are optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or —CO$_2$H;

R$^4$ is hydrogen, alkyl of 1-6 carbon atoms, or phenylalkyl of 7-10 carbon atoms wherein the phenyl moiety of the phenylalkyl group is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, and —CO$_2$H;

R$^2$ and R$^5$ are each independently hydrogen, formyl, alkanoyl of 2-7 carbon atoms, phenylulkanoyl of 8-11 carbon atoms, phenyloyl, or CO$_2$R$^6$ wherein the phenyl moiety of the phenylalkanoyl and phenyloyl groups are optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, and —CO$_2$H;

R$^6$ is alkyl of 1-6 carbon atoms, phenylalkyl of 7-10 carbon atoms, allyl, fluorenylmethyl, or phenyl; wherein the phenyl moiety of the phenyl and phenylalkyl groups are optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino or —CO$_2$H;

m is 0-4;
n is 0-4;
p is 0-1;
q is 0-4;
r is 0-4; and
s is 0-4 or a pharmaceutically acceptable salt thereof.

2. A compound of claim 1 where p is 0 or a pharmaceutically acceptable salt thereof.

3. A compound of claim 1 where p is 0, m is 0, and n is 1-2, or a pharmaceutically acceptable salt thereof.

4. A compound of claim 1 which is rapamycin-42,42'-diester with N-[(phenylmethoxy) carbonyl]-L-glutamic acid or a pharmaceutically acceptable salt thereof.

5. A compound of claim 1 which is rapamycin 42-42'-diester with N-[(phenylmethoxycarbonyl)]-L-aspartic acid or a pharmaceutically acceptable salt thereof.

6. A method of treating transplantation rejection, host vs. graft disease, autoimmune diseases, and diseases of inflammation in a mammal by administering to said mammal an immunosuppressive amount of a compound having the formula

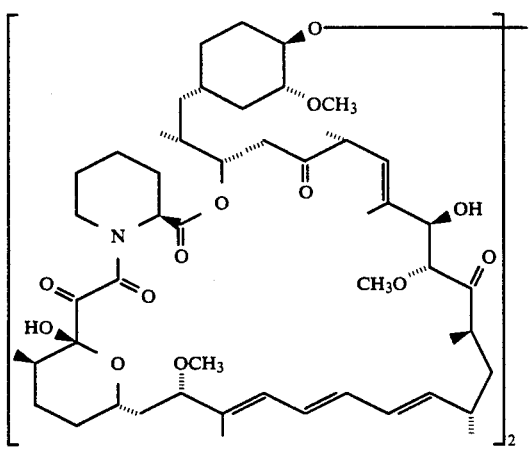

wherein R¹ is

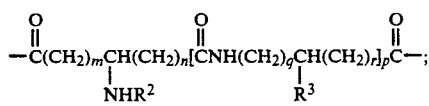

R³ is hydrogen, alkyl of 1-6 carbon atoms, phenylakyl of 7-10 carbon atoms, $(CH_2)_sNR^4R^5$, aminoalkyl of 1-4 carbon atoms, hydroxyalkyl of 1-4 carbon atoms, guanylalkyl of 2-4 carbon atoms, mercaptoalkyl of 1-4 carbon atoms, alkylthioalkyl of 2-6 carbon atoms, indolylmethyl, hydroxyphenylmethyl, imidazolylmethyl or phenyl; wherein the phenyl moiety of the phenyl and phenylalkyl groups are optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or —CO₂H;

R⁴ is hydrogen, phenylalkyl of 1-6 carbon atoms, or aralkyl of 7-10 carbon atoms wherein the phenyl moiety of the phenylalkyl group is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, and —CO₂H;

R² and R⁵ are each independently hydrogen, formyl, alkanoyl of 2-7 carbon atoms, phenylalkanoyl of 8-11 carbon atoms, phenyloyl, or CO₂R⁶ wherein the phenyl moiety of the phenylalkanoyl and phenyloyl groups are optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, and —CO₂H;

R⁶ is phenylalkyl of 1-6 carbon atoms, arylalkyl of 7-10 carbon atoms, allyl, fluorenylmethyl, or phenyl; wherein the phenyl moiety of the phenyl and phenylalkyl groups are optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino or —CO₂H;

m is 0-4;
n is 0-4;
p is 0-1;
q is 0-4;
r is 0-4; and
s is 0-4 or a pharmaceutically acceptable salt thereof.

7. A pharmaceutical composition comprising an immunosuppressive amount of a compound having the formula

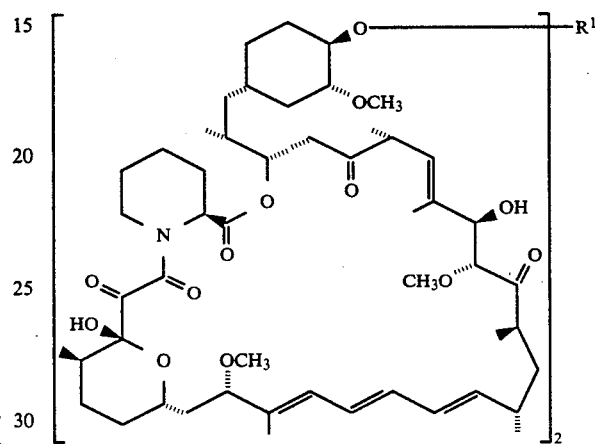

wherein R¹ is

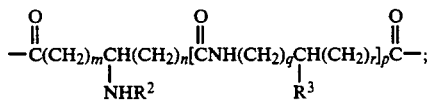

R³ is hydrogen, alkyl of 1-6 carbon atoms, phenylakyl of 7-10 carbon atoms, $(CH_2)_sNR^4R^5$, aminoalkyl of 1-4 carbon atoms, hydroxyalkyl of 1-4 carbon atoms, guanylalkyl of 2-4 carbon atoms, mercaptoalkyl of 1-4 carbon atoms, alkylthioalkyl of 2-6 carbon atoms, indolylmethyl, hydroxyphenylmethyl, imidazolylmethyl or phenyl; wherein the phenyl moiety of the phenyl and phenylalkyl groups are optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or —CO₂H;

R⁴ is hydrogen, alkyl of 1-6 carbon atoms, or phenylalkyl of 7-10 carbon atoms wherein the phenyl moiety of the phenylalkyl group is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, and —CO₂H;

R² and R⁵ are each independently hydrogen, formyl, alkanoyl of 2-7 carbon atoms, phenylalkanoyl of 8-11 carbon atoms, phenyloyl, or CO₂R⁶ wherein the phenyl moiety of the phenylalkanoyl and phenyloyl groups are optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, and —CO$_2$H;

R$^6$ is alkyl of 1-6 carbon atoms, phenylalkyl of 7-10 carbon atoms, allyl, fluorenylmethyl, or phenyl; wherein the phenyl moiety of the phenyl and phenylalkyl groups are optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino or —CO$_2$H;

m is 0-4;
n is 0-4;
p is 0-1;
q is 0-4;
r is 0-4; and
s is 0-4 or a pharmaceutically acceptable salt thereof and a pharmaceutical carrier.

* * * * *